United States Patent
Klausener et al.

(10) Patent No.: US 12,410,158 B2
(45) Date of Patent: Sep. 9, 2025

(54) PROCESS FOR PREPARING ANTHRANILIC DIAMIDES AND INTERMEDIATES THEREOF

(71) Applicant: PI INDUSTRIES LTD., Udaipur-Rajasthan (IN)

(72) Inventors: Alexander Klausener, Pulheim (DE); Shrikant Bhausaheb Kanawade, Nashik-Maharashtra (IN); Vijay Kumar Salvi, Udaipur-Rajasthan (IN); Suresh Kumar Sythana, Rajendra Nagar-Hyderabad (IN); Yuvraj Navnath Kale, Dist-Ahmednagar-Maharashtra (IN); Pramod Subhash Nagle, Jalgaon-Maharashtra (IN); Deepak Shankar Panmand, Dist: Ahmednagar-Maharashtra (IN)

(73) Assignee: PI INDUSTRIES LTD., Udaipur-Rajasthan (IN)

( * ) Notice: Subject to any disclaimer, the term of this patent is extended or adjusted under 35 U.S.C. 154(b) by 791 days.

(21) Appl. No.: 17/310,673

(22) PCT Filed: Feb. 14, 2020

(86) PCT No.: PCT/IB2020/051227
§ 371 (c)(1),
(2) Date: Aug. 17, 2021

(87) PCT Pub. No.: WO2020/170092
PCT Pub. Date: Aug. 27, 2020

(65) Prior Publication Data
US 2022/0144814 A1    May 12, 2022

(30) Foreign Application Priority Data

Feb. 18, 2019  (IN) .............................. 201911006381

(51) Int. Cl.
C07D 409/12    (2006.01)
C07D 231/14    (2006.01)
C07D 403/06    (2006.01)

(52) U.S. Cl.
CPC ......... *C07D 409/12* (2013.01); *C07D 231/14* (2013.01); *C07D 403/06* (2013.01)

(58) Field of Classification Search
None
See application file for complete search history.

(56) References Cited

FOREIGN PATENT DOCUMENTS

| WO | 00/58288 A1 | 10/2000 |
| WO | 00/59868 A1 | 10/2000 |

(Continued)

*Primary Examiner* — Adam C Milligan
*Assistant Examiner* — Jed A Kucharczk
(74) *Attorney, Agent, or Firm* — Lippes Mathias LLP

(57) ABSTRACT

The present invention relates a novel process for preparing a compound of Formula I,

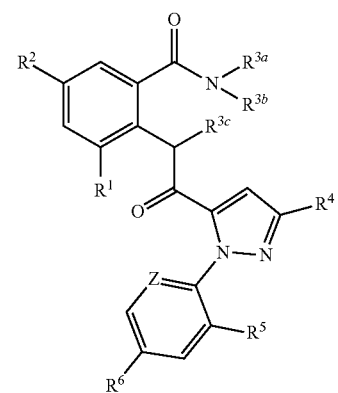

wherein, $R^1$, $R^2$, $R^{3a}$, $R^{3b}$, $R^{3c}$, $R^4$, $R^5$, $R^6$, $R^7$ and Z are as defined in the description.

The process comprises a novel and inventive step of converting a dione of Formula II into an isatoic anhydride of Formula V in a single step.

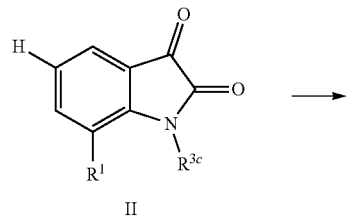

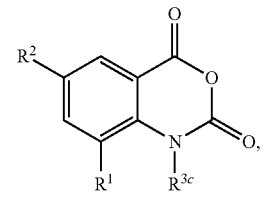

wherein, $R^2$ is F, Cl, Br or I; $R^1$, $R^{3a}$, $R^{3b}$, $R^{3c}$, $R^4$, $R^5$, $R^6$, $R^7$ and Z are as defined in the description.

17 Claims, No Drawings

(56) References Cited

FOREIGN PATENT DOCUMENTS

| | | |
|---|---|---|
| WO | 03/015518 A1 | 2/2003 |
| WO | 03/015519 A1 | 2/2003 |
| WO | 2004/011447 A1 | 2/2004 |
| WO | 2004/067528 A1 | 8/2004 |
| WO | 2004/111030 A1 | 12/2004 |
| WO | 2005/077934 A1 | 8/2005 |
| WO | 2006/062978 A1 | 6/2006 |
| WO | 2008/010897 A2 | 1/2008 |
| WO | 2008/070158 A1 | 6/2008 |
| WO | 2008/082502 A2 | 7/2008 |
| WO | 2009/006061 A2 | 1/2009 |
| WO | 2009/061991 A1 | 5/2009 |
| WO | 2009/085816 A1 | 7/2009 |
| WO | 2010/069502 A2 | 6/2010 |
| WO | 2011/157664 A1 | 12/2011 |
| WO | 2012/103436 A1 | 8/2012 |
| WO | 2013/030100 A1 | 3/2013 |

PROCESS FOR PREPARING ANTHRANILIC DIAMIDES AND INTERMEDIATES THEREOF

This application is a National Stage Entry of International Application No. PCT/IB2020/051227, filed Feb. 14, 2020, and entitled "A PROCESS FOR PREPARING ANTHRANILIC DIAMIDES AND INTERMEDIATES THEREOF;" which claims priority to Indian Application No. 201911006381, filed Feb. 18, 2019, and entitled "A PROCESS FOR PREPARING ANTHRANILIC DIAMIDES AND INTERMEDIATES THEREOF," the contents of which are incorporated by reference herein.

FIELD OF THE INVENTION

The present invention relates to a novel process for preparing anthranilic diamides involving the conversion of isatins into isatoic anhydrides. The present invention also relates to a novel process for preparing isatoic anhydrides useful in the process for preparing anthranilic diamides.

BACKGROUND OF THE INVENTION

WO2003015518, WO2003015519, WO2004067528, WO2005077934 and WO20100069502 disclose the use of anthranilic diamides for controlling invertebrate pests such as arthropods.

Several patent documents, for example WO2004011447, WO2004111030, WO2006062978, WO2008010897 and WO2012103436 disclose processes for preparing anthranilic diamides and suitable intermediates.

However, the processes described in the above mentioned literature are laborious or are lacking from sufficient selectivity, and there is still need to find a simple, efficient and industrially economical process for the preparation of anthranilic diamides.

OBJECT AND SUMMARY OF THE INVENTION

It is the objective of the present invention to provide an industrially amenable and convenient process for the preparation of anthranilic diamides of Formula I.

Surprisingly, the present invention provides a solution to this objective by providing a novel process that allows the preparation of anthranilic diamides, overcoming at least one of the shortcomings of the processes described in the prior art.

The said objective was achieved according to the present invention by providing a novel process for preparing a compound of Formula I,

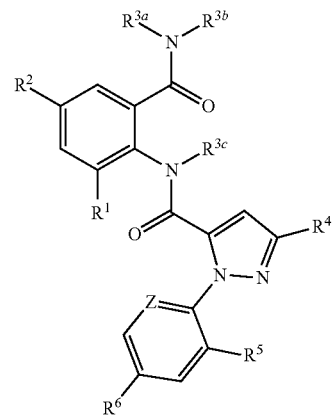

wherein,
$R^1$ is $CH_3$, Br or Cl;
$R^2$ is F, Cl, Br, I or CN;
$R^{3a}$ and $R^{3b}$ are independently H, $C_1$-$C_4$ alkyl or $C_3$-$C_6$ cycoalkyl-$C_1$-$C_4$ alkyl;
$R^{3c}$ is H or $C_1$-$C_4$ alkyl;
$R^4$ is Cl, Br, $CF_3$, $OCF_2H$, $OCH_2CF_3$,

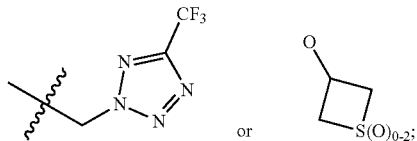

$R^5$ is F, Cl or Br;
$R^6$ is H, F or Cl;
Z is $CR^7$ or N; and
$R^7$ is H, F, Cl or Br.

The process according to this invention comprises the step of obtaining a dione of Formula II from an aniline III and chloral hydrate IV, and converting the dione of Formula II into an isatoic anhydride of Formula V in a single step. The conversion of the dione of Formula II into an isatoic anhydride of Formula V is novel and inventive as both the oxidation and the halogenation reactions are carried out in a single step.

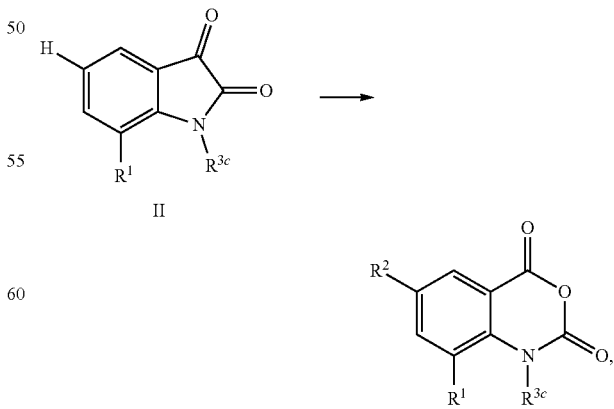

wherein, $R^2$ is F, Cl, Br or I; $R^1$ and $R^{3c}$ are as defined hereinabove.

The isatoic anhydride of Formula V and an amine of Formula VI are reacted to obtain a compound of Formula VII that are then further reacted with a compound of Formula VIII to finally obtain the compound of Formula I,

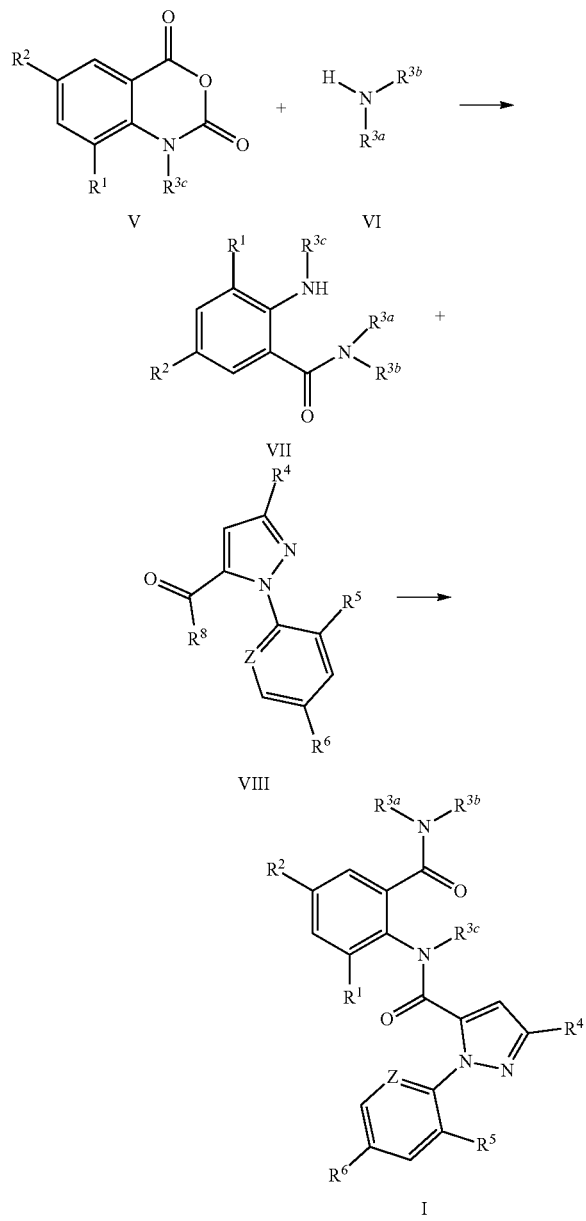

wherein, $R^1$, $R^2$, $R^{3a}$, $R^{3b}$, $R^{3c}$, $R^4$, $R^5$, $R^6$ and Z are as defined for Formula I; and $R^8$ is OH, Cl, X or O—$C_1$-$C_4$ alkyl.

DETAILED DESCRIPTION OF THE INVENTION

General Definitions

The definitions provided herein for the terminologies used in the present disclosure are for illustrative purpose only and in no manner limit the scope of the present invention disclosed in the present disclosure.

As used herein, the terms "comprises", "comprising", "includes", "including", "has", "having", "contains", "containing", "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components or elements, in addition to those literally disclosed, provided that these additional materials, steps, features, components or elements do not materially affect the basic and novel characteristic(s) of the claimed invention. The term "consisting essentially of" occupies a middle ground between "comprising" and "consisting of".

Further, unless expressly stated to the contrary, "or" refers to an inclusive "or" and not to an exclusive "or". For example, a condition A "or" B is satisfied by any one of the following: A is true (or present) and B is false (or not present), A is false (or not present) and B is true (or present), and both A and B are true (or present).

Also, the indefinite articles "a" and "an" preceding an element or component of the present invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

Carbon-based radical refers to a monovalent molecular component comprising a carbon atom that connects the radical to the remainder of the chemical structure through a single bond. Carbon-based radicals can optionally comprise saturated, unsaturated and aromatic groups, chains, rings and ring systems, and heteroatoms. Although carbon-based radicals are not subject to any particular limit in size, in the context of the present invention they typically comprise 1 to 16 carbon atoms and 0 to 3 heteroatoms. Of note are carbon-based radicals selected from $C_1$-$C_6$ alkyl, $C_1$-$C_6$ haloalkyl and phenyl optionally substituted with 1-3 substituents selected from $C_1$-$C_3$ alkyl, halogen and nitro.

The meaning of various terms used in the description shall now be illustrated.

The term "alkyl", used either alone or in compound words such as "alkylthio" or "haloalkyl" or —N(alkyl) or alkylcarbonylalkyl or alkylsuphonylamino includes straight-chain or branched $C_1$ to $C_{24}$ alkyl, preferably $C_1$ to $C_{15}$ alkyl, more preferably $C_1$ to $C_{10}$ alkyl, most preferably $C_1$ to $C_6$ alkyl. Representative examples of alkyl include methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl or the different isomers. If the alkyl is at the end of a composite substituent, as, for example, in alkylcycloalkyl, the part of the composite substituent at the start, for example the cycloalkyl, may be mono- or polysubstituted identically or differently and independently by alkyl. The same also applies to composite substituents in which other radicals, for example alkenyl, alkynyl, hydroxyl, halogen, carbonyl, carbonyloxy and the like, are at the end.

The term "cycloalkyl" means alkyl closed to form a ring. Representative examples include but are not limited to cyclopropyl, cyclobutyl, cyclopentyl and cyclohexyl. This definition also applies to cycloalkyl as a part of a composite substituent, for example cycloalkylalkyl etc., unless specifically defined elsewhere.

The present invention relates to a process for preparing a compound of Formula I,

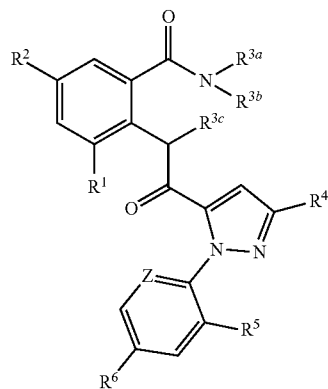

wherein, $R^1$ is $CH_3$, Br or Cl;

$R^2$ is F, Cl, Br, I or CN;

$R^{3a}$ and $R^{3b}$ are independently H, $C_1$-$C_4$ alkyl or $C_3$-$C_6$ cycoalkyl-$C_1$-$C_4$ alkyl;

$R^{3c}$ is H or $C_1$-$C_4$ alkyl;

$R^4$ is Cl, Br, $CF_3$, $OCF_2H$, $OCH_2CF_3$, or

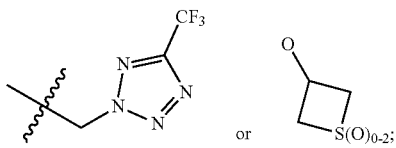

$R^5$ is F, Cl or Br;

$R^6$ is H, F or Cl;

Z is $CR^7$ or N; and $R^7$ is H, F, Cl or Br.

The process of the present invention is described herein after.

Initially, a dione of Formula II is obtained by reacting an aniline of Formula III and chloral hydrate IV,

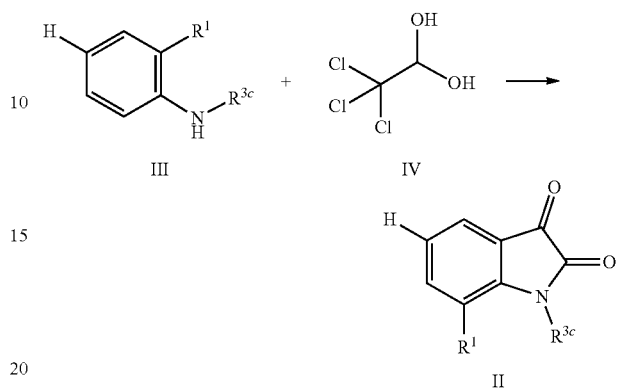

wherein, $R^1$ and $R^{3c}$ are as defined herein above.

In one embodiment, the compound of Formula III and chloral hydrate of Formula IV are reacted in the presence of one or more suitable reagent including but not limiting to hydrochloric acid, sulfuric acid, acetic acid, trifluoroacetic acid, nitric acid and sodium sulphate in one or more solvent/s at a temperature ranging from 25° C. to 100° C., followed by stirring with mineral acid including but not limiting to sulfuric acid, hydrochloric acid and nitric acid at 0° C. to 45° C. to obtain the dione of Formula II.

In another embodiment, the oxime of Formula IIIa is formed by reacting the compound of Formula III and chloral hydrate of Formula IV or hydroxylamine in the presence of one or more suitable reagent including but not limiting to hydrochloric acid, sulfuric acid, acetic acid trifluoroacetic acid, nitric acid and sodium sulphate and one or more solvent/s at a temperature ranging from 15° C. to 150° C.,

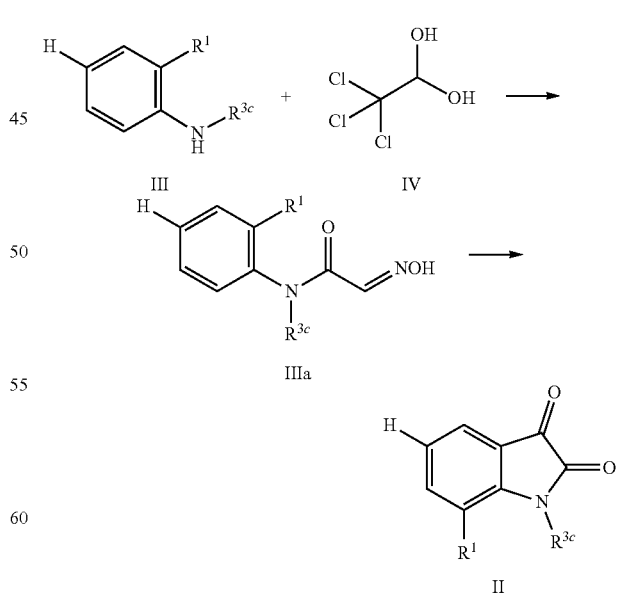

wherein, $R^1$ and $R^{3c}$ are as defined herein above.

The solvent useful in this step includes but is not limited to aliphatic hydrocarbons such as hexane, heptane, octane, nonane, decane, dodecane and the like; alicyclic hydrocarbons such as cycloalkanes: cyclopropane, cyclobutane, cyclopentane, cyclohexane, cycloheptane, cyclooctane, and the like; aromatic hydrocarbons such as toluene, xylene, mesitylene, benzene and the like; ethers such as diisopropyl ether, t-butyl methyl ether, tetrahydrofuran, 2-methyl tetrahydrofuran, methyl alcohol, ethyl alcohol, acetone, dioxane, monoglyme, diglyme, methoxy-methane, methoxy-ethane, ethoxy-ethane, di-methoxyethane, di-ethoxyethane and the like; halogenated hydrocarbons such as dichloromethane, chloroform, dichloroethane and like; ethers, polar aprotic solvents such as N,N-dimethylmethanamide, dimethyl sulfoxide, N-methyl-2-pyrrolidone, 1,3-dimethyl-3,4,5,6-tetrahydro-2(1H)-pyrimidinone, hexamethylphosphoramidem, 1,3-dimethyl-2-imidazolidinone and the like; and water.

The oxime of Formula IIIa formed is then converted into the compound of Formula II by using mineral acid including but not limiting to sulfuric acid, hydrochloric acid and nitric acid and stirring within a temperature ranging from 0° C. to 150° C.

The obtained dione of Formula II is converted into an isatoic anhydride of Formula V using a suitable halogenating reagent, one or more suitable oxidizing reagent/s and one or more suitable solvent at a temperature ranging from 0° C. to 250° C.,

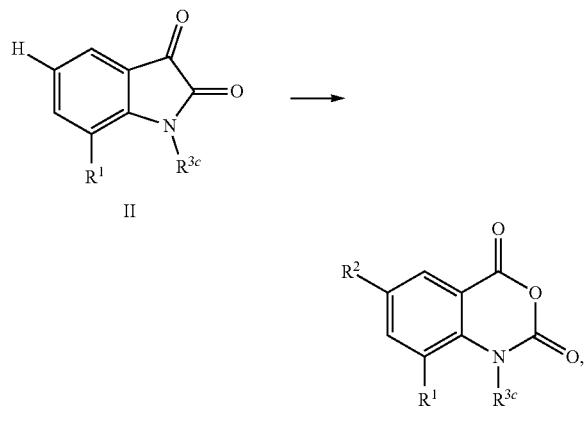

wherein, $R^2$ is F, Cl, Br or I; $R^1$ and $R^{3c}$ are as defined herein above.

The halogenating reagent useful for converting the dione of Formula II into the isatoic anhydride of Formula V includes but is not limited to HX, NaX, KX, $CuX_2$, $MgX_2$, CsX, $ZnX_2$, $SOCl_2$, $SO_2Cl_2$, $COCl_2$, $X_2$, $C(=O)(OCl_3)_2$, t-BuOCl, NaOCl, Chloramine-T, N-halosuccinamides, $POX_3$, $PX_3$, $PX_5$ or metal halides; wherein X is Cl, Br, I or F.

The oxidizing reagents useful for converting the dione of Formula II into the isatoic anhydride of Formula V include but is not limited to hydrogen peroxide, t-butyl-hydroperoxide, tungstic peroxide, m-chloroperbenzoic acid, benzoyl peroxide, hypohalous acid, ceric ammonium nitrate, hypoceric ammonium nitrate, oxone, periodic acid, hydrogen peroxide urea-adduct, sodium perborate, pyridinium chlorochromate and dimethyl sulfoxide.

The solvent useful for converting the dione of Formula II into the isatoic anhydride of Formula V include but is not limited to an organic acid selected from the group consisting of formic acid, acetic acid, triflic acid, butyric acid, propionic acid, benzoic acid, m-chlorobenzoic acid, carbonic acid, glycolic acid, and trifluoroacetic acid.

Alternatively, the solvents useful for converting the dione of Formula II into the isatoic anhydride of Formula V include but is not limited to a mixture of said organic acid/s with one or more solvent/s selected from the group comprising of aliphatic hydrocarbons such as hexane, heptane, octane, nonane, decane, dodecane and the like; alicyclic hydrocarbons such as cycloalkanes: cyclopropane, cyclobutane, cyclopentane, cyclohexane, cycloheptane, cyclooctane, and the like; aromatic hydrocarbons such as toluene, xylene, mesitylene, benzene and the like; ethers such as diisopropyl ether, t-butyl methyl ether, tetrahydrofuran, 2-methyl tetrahydrofuran, methyl alcohol, ethyl alcohol, acetone, dioxane, monoglyme, diglyme, methoxy-methane, methoxy-ethane, ethoxy-ethane, di-methoxyethane, di-ethoxyethane and the like; halogenated hydrocarbons such as dichloromethane, chloroform, dichloroethane and the like; polar aprotic solvents such as N,N-dimethylmethanamide, dimethyl sulfoxide, N-methyl-2-pyrrolidone, 1,3-dimethyl-3,4,5,6-tetrahydro-2(1H)-pyrimidinone, hexamethylphosphoramidem, 1,3-dimethyl-2-imidazolidinone and the like; and water.

In one embodiment, the step of converting the dione of Formula II into the isatoic anhydride of Formula V is carried out by mixing i) a mixture of the halogenating reagent and the oxidizing reagent, and ii) a mixture of the dione of Formula II and the solvent, at a temperature ranging from 10 to 50° C. and then by heating at a temperature ranging from 15-150° C.

In another embodiment, the step of converting the dione of Formula II into the isatoic of Formula V is carried out by mixing i) the halogenating reagent, and ii) the oxidizing reagent separately in either sequence with iii) a mixture of the dione of Formula II and the solvent, at a temperature ranging from 10 to 50° C., followed by heating at a temperature ranging from 15-150° C.

In the next step, the isatoic anhydride of Formula V and an amine of Formula VI are reacted to obtain a compound of Formula VII,

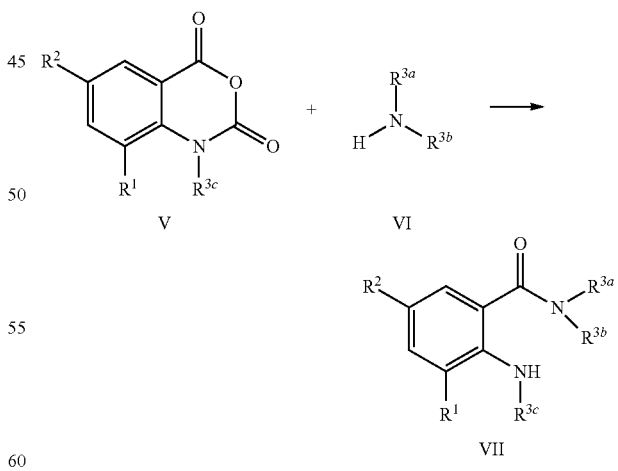

wherein, $R^2$ is F, Cl, Br or I; $R^1$, $R^2$, $R^{3a}$, $R^{3b}$ and $R^{3c}$ are as defined herein before.

The amine of Formula VI may be used in aqueous form or a gaseous form. For example, when $R^{3c}$ is methyl, then methyl amine is used for the preparation of compound of Formula VII, wherein $R^{3c}$ is methyl; in this case methyl amine may be used in gaseous form or may be used as a solution in water or one or more solvent/s.

The solvents being useful for this reaction are preferably selected from the group comprising of aliphatic hydrocarbons such as hexane, heptane, octane, nonane, decane, dodecane and the like; alicyclic hydrocarbons such as cycloalkanes: cyclopropane, cyclobutane, cyclopentane, cyclohexane, cycloheptane, cyclooctane, and the like; aromatic hydrocarbons such as toluene, xylene, mesitylene, benzene and the like; ethers such as diisopropyl ether, t-butyl methyl ether, tetrahydrofuran, 2-methyl tetrahydrofuran, methyl alcohol, ethyl alcohol, acetone, dioxane, monoglyme, diglyme, methoxy-methane, methoxy-ethane, ethoxy-ethane, di-methoxyethane, di-ethoxyethane and the like; halogenated hydrocarbons such as dichloromethane, chloroform, dichloroethane and like; ethers, polar aprotic solvents such as N,N-dimethylmethanamide, dimethyl sulfoxide, N-methyl-2-pyrrolidone, 1,3-dimethyl-3,4,5,6-tetrahydro-2(1H)-pyrimidinone, hexamethylphosphoramidem, 1,3-dimethyl-2-imidazolidinone and the like; and water.

The conversion of the isatoic anhydride of Formula V and the amine of Formula VI may further require the presence of a suitable reagent which includes but is not limited to formic acid, acetic acid, triflic acid, benzoic acid, m-chlorobenzoic acid, butyric acid, propionic acid, glycolic acid, trifluoroacetic acid, para-toluene sulfonic acid, methane sulfonic acid, butyric acid, citric acid, oxalic acid, malonic acid, maleic acid, gallic acid, tartaric acid, ascorbic acid, hydrochloric acid, hydroiodic acid, sulphuric acid, nitric acid, phosphoric acid, perchloric acid, boronic acids, amberlysts, aluminum chloride, zinc chloride, boron trifluoro ether, zinc oxide, titanium tetrachloride, tin chloride and combinations thereof.

The temperature conditions employed for the conversion of the isatoic anhydride of Formula V and the amine of Formula VI range from 0° C. to 150° C., depending on the solvent used and the amine reactant employed.

In one embodiment, the compound of Formula V is isolated.

In another embodiment, the compound of Formula V is not isolated.

In one embodiment, the isatoic anhydride of Formula V, wherein in $R^2$ is F, Cl, Br or I, can be converted into a compound of Formula V, wherein $R^2$ is CN. The compound of Formula VII, wherein in $R^2$ is F, Cl, Br or I, can be converted into a compound of Formula VII, wherein in $R^2$ is F, Cl, Br or I, by cyanation. The cyanation of the isatoic anhydride of Formula V and or the compound of Formula VII can be carried out by the process reported in WO2008010897, WO2008070158, WO2009085816, WO2009061991, WO2009006061 and WO2008082502.

Finally, the compound of Formula VII and a compound of Formula VIII are reacted to obtain the compound of Formula I,

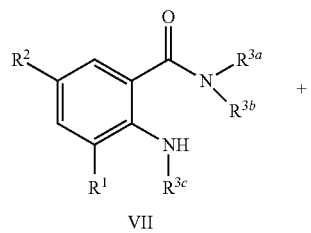

VII

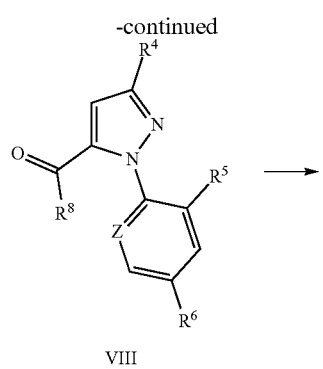

VIII

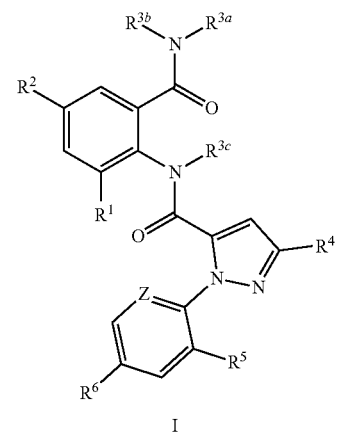

I wherein, $R^1$, $R^2$, $R^{3a}$, $R^{3b}$, $R^{3c}$, $R^4$, $R^5$, $R^6$ and Z are as define herein before; $R^8$ is OH, Cl, or O—$C_1$-$C_4$ alkyl.

The compound of Formula VIII can be obtained by either of the processes disclosed in WO2003015518, WO20030155519, WO2011157664 and WO2013030100.

The present invention also relates to a process for preparing a compound of Formula VII,

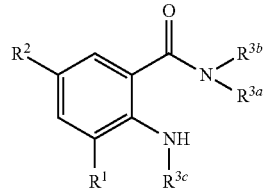

VII wherein,
$R^1$ is $CH_3$, Br or Cl;
$R^2$ is F, Cl, Br, I or CN;
$R^{3a}$ and $R^{3b}$ are independently H, $C_1$-$C_4$ alkyl or $C_3$-$C_6$ cycoalkyl-$C_1$-$C_4$ alkyl; and
$R^{3c}$ is independently H or $C_1$-$C_4$ alkyl.

The process for preparing the compound of Formula VII is basically the same as described herein before.

The present invention further relates to a process for preparing a compound of Formula V,

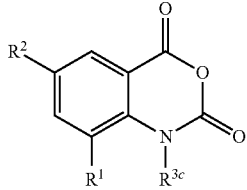

wherein,
R¹ is CH₃, Br or Cl;
R² is F, Cl, Br, I or CN; and
R³ᶜ is H or C₁-C₄ alkyl.

The process for preparing the compound of Formula V is described herein before.

All or any of the process steps of the present invention may be carried out in continuous, semi-continuous, flow or batch form. Particularly, the process steps of the present invention are carried out in semi-continuous form.

All or any of the process steps may be carried out at a pressure ranging from 0.5 kg/cm² to 250 kg/cm².

The present inventions shall now be described in light of the following non-limiting examples.

Example 1

Step A: Preparation of 2-(hydroxyimino)-N-(o-tolyl)acetamide

Into a solution of o-toluidine (75 g, 700 mmol) in water (170 mL), hydrochloric acid (73 g, 700 mmol, 35% w/w) was slowly added, followed by the addition of a solution of anhydrous sodium sulphate (636 g, 4478 mmol) in water (800 mL). The resulting reaction mixture was heated to 55° C. Then an aqueous solution of hydroxylamine hydrochloride (73 g, 1050 mmol) in water (280 mL) was slowly added, followed by the addition of chloral hydrate (125 g, 757 mmol) in water (270 mL). The reaction mixture was maintained at 55° C. for 12 h. After completion of the reaction, the reaction mixture was cooled to 20° C. and stirred for 1 h. The solid product was filtered and washed two times with water (100 mL) to obtain 2-(hydroxyimino)-N-(o-tolyl)acetamide (95 g, 531 mmol, Yield: 76%).

¹H-NMR (400 MHz, DMSO-d₆) δ 12.16 (s, 1H), 9.47 (bs, 1H), 7.66 (s, 1H), 7.45-7.47 (d, J=7.8 Hz, 1H), 7.19-7.24 (dd, J=7.4 Hz & 0.6 Hz, 1H), 7.14-7.18 (td, J=7.6 Hz & 1.6 Hz, 1H), 7.08-7.13 (td, J=7.4 Hz & 1.3 Hz, 1H), 2.22 (s, 3H) MS: m/z=179.05 [M+H].

Step B-1: Preparation of 7-methylindoline-2,3-dione 2-(Hydroxyimino)-N-(o-tolyl)acetamide (92 g, 485 mmol) was added lot wise to a solution of sulphuric acid (333 g, 3397 mmol) at 0-5° C. The temperature was slowly allowed to raise to 30° C., and the reaction mixture was stirred for 12 h. Then the reaction mixture was slowly poured into water (1800 mL), and the precipitated solid product was filtered off and washed with water (200 mL) to obtain 7-methylindoline-2,3-dione (71.5 g, 485 mmol, Yield: 91%).

¹H-NMR (400 MHz, DMSO-d₆) δ 11.08 (s, 1H), 7.42 (d, J=7.6 Hz, 1H), 7.31 (d, J=7.6 Hz, 1H), 6.96 (t, J=7.6 Hz, 1H), 2.17 (s, 3H)
MS: m/z=162.00 [M+H].

Step B-2: Preparation of 7-methylindoline-2,3-dione 2-(Hydroxyimino)-N-(o-tolyl)acetamide (10 g, 15.8 mmol) was added lot wise to a solution of sulphuric acid (36.2 g, 369 mmol) and 1,2-dichloroethane (50 mL) at 0-5° C. The temperature was allowed to rise to 30° C., and the reaction mixture was stirred for 12 h. Then the reaction mixture was slowly poured into water (190 mL). The dichloroethane was removed under reduced pressure, and the remaining suspended solid product was filtered off and washed with water (20 mL) to obtain 7-methylindoline-2,3-dione (8.1 g, 50 mmol, Yield: 95%).

Step C-1: Preparation of 6-chloro-8-methyl-2H-benzo[d][1,3]oxazine-2,4(1H)-dione 7-Methylindoline-2,3-dione (50 g, 261 mmol) and acetic acid (421 g) were mixed at 25° C. to obtain a suspension. To this suspension, hydrogen peroxide (163 g, 1437 mmol, 30% w/w) was added slowly at 25° C. within 15 min under stirring, followed by the addition of conc. hydrochloric acid (82.0 g, 653 mmol, 29% w/w) at a temperature between 30 and 40° C. within 45 min. The reaction mixture was stirred for 3 h at 40° C. The reaction mass was then heated at 70° C. for 4 h. The reaction mass was cooled to 25° C. and then poured slowly onto crushed ice-water mixture (415 g), under stirring at 0-5° C. The solid that was obtained by this procedure was filtered, washed with cold water (100 mL) and dried under vacuum to obtain crude compound of 6-chloro-8-methyl-2H-benzo[d][1,3]oxazine-2,4(1H)-dione (46 g, 261 mmol, Yield: 83%).

Step C-2: Preparation of 6-chloro-8-methyl-2H-benzo[d][1,3]oxazine-2,4(1H)-dione 7-Methylindoline-2,3-dione (20 g, 116 mmol) and acetic acid (187 g, 3127 mmol) were mixed at 25° C. to obtain a suspension. To this, hydrogen peroxide (Lot-1) (18 g, 232 mmol) was added slowly within 5 min at the same temperature, followed by the addition of hydrochloric acid (51.0 g, 406 mmol) within 30 min at 15° C. The resulting reaction mass was stirred for 2 h at 25° C. Then hydrogen peroxide (Lot-2) (27 g, 348 mmol) was slowly added within 30 min at 15° C. and under stirring. The reaction mixture was heated to 60° C. and stirred for 6 h. Hydrogen peroxide (Lot-3) (12 g, 174 mmol) was again added slowly at 20° C. and under stirring. The reaction mixture was heated to 60° C. and stirred for further 2 h. The reaction was slowly quenched by pouring it into chilled water (930 g) at 0° C. The resulting mixture was stirred for 1 h at 0° C. and filtered to obtain a solid material. The solid was washed with chilled water (40 g) and dried under reduced pressure at 50° C. for overnight to obtain 6-chloro-8-methyl-2H-benzo[d][1,3]oxazine-2,4(1H)-dione (15.4 g, 72.8 mmol, Yield: 63%).

¹H-NMR (400 MHz, DMSO-d₆) δ 11.17 (s, 1H), 7.73 (dd, J=2.4 Hz & 0.5 Hz, 1H), 7.69 (dd, J=2.4 Hz & 0.7 Hz, 1H), 2.34 (s, 3H).
MS: m/z=209.90 [M−H].

Step C-3: Preparation of 6-chloro-8-methyl-2H-benzo[d][1,3]oxazine-2,4(1H)-dione 7-methylindoline-2,3-dione (50 g, 298 mmol) and acetic acid (483 g, 8047 mmol) were mixed at 5° C. to obtain a suspension. Hydrogen peroxide (Lot-1) (69 g, 894 mmol) was added under stirring slowly to this suspension at 5° C. for 15 min. Then hydrochloric acid (Lot-1) (56 g, 447 mmol) was added very slowly and under stirring at 5° C. for 160 min. The resulting reaction mass was stirred further for 2.5 h at 10° C., then allowed to warm up to 20° C. and stirred for further 23 h. Hydrogen peroxide (Lot-2) (26 g, 313 mmol) was added at 10° C. for 15 min under stirring, and then HCl (Lot-2) (18 g, 158 mmol) was added under stirring very slowly over a period of 30 min at 10° C. The reaction mass was stirred at 40° C. for 3 h, filtered under reduced pressure. The filter cake which was obtained was washed three times with water (600 mL) and dried under reduced pressure at 25° C. for 16 h. The crude solid was then dried in an oven under reduced pressure (760 mm Hg) at 55° C. for 16 h to obtain 6-chloro-8-methyl-2H-benzo[d][1,3]oxazine-2,4(1H)-dione (52.70 g, 298 mmol, Yield: 84%).

Step C-4: Preparation of 6-Bromo-8-methyl-2H-benzo[d][1,3]oxazine-2,4(1H)-dione

To the suspension of 7-Methylindoline-2,3-dione (10 g, 60.0 mmol) and acetic acid (100 g), hydrogen peroxide (27 g, 360 mmol) was added at 25-30° C. Hydrobromic acid (11 g, 57.1 mmol) was added at a temperature between 15-25° C. in 1 h. After stirring for 2 h at 25-30° C., sulphuric acid (0.3 g, 3.0 mmol) was added and the reaction mass was heated to 45-50° C. and stirred for 8 h. The temperature was slowly raised to 70-75° C. and stirred further for 2 h. After completion of the reaction, the reaction mixture was cooled to 25° C. and poured slowly over crushed ice-water mixture (500 g) under constant stirring at 0-5° C. The solid obtained was filtered, washed with cold water (100 g) and dried under reduced pressure to obtain crude 6-Bromo-8-methyl-2H-benzo[d][1,3]oxazine-2,4(1H)-dione (11.5 g, 45 mmol, Yield: 75%).
$^1$H-NMR (400 MHz, DMSO-$d_6$) δ 11.16 (s, 1H), 7.83 (d, J=2.4 Hz, 1H), 7.78 (d, J=2.4 Hz, 1H), 2.31 (s, 3H) LCMS: m/z=254 [M-2H].

Step D-1: Preparation of 2-amino-5-chloro-N,3-dimethylbenzamide

A suspension of 6-chloro-8-methyl-2H-benzo[d][1,3]oxazine-2,4(1H)-dione (17 g, 80 mmol), acetic acid (10 g, 160 mmol) and ethyl acetate (200 mL) was cooled under stirring to 0° C. Methylamine gas was bubbled through this stirred suspension at 0° C. for 15 min (pH=9 to 10). The resulting reaction mixture was then allowed to warm to 25° C. and stirred for further 3 h. After completion of the reaction, the reaction mixture was poured into water (200 g) and extracted twice with ethyl acetate (200 g). The combined ethyl acetate layers were dried over anhydrous sodium sulphate, filtered and distilled under reduced pressure to obtain crude 2-amino-5-chloro-N,3-dimethylbenzamide (12.0 g, 60.4 mmol, Yield: 75%).
$^1$H-NMR (400 MHz, DMSO-$d_6$) δ 8.31 (d, J=4.2 Hz, 1H), 7.37-7.38 (d, J=2.4 Hz, 1H), 7.10-7.12 (d, J=2.4 Hz, 1H), 6.35 (s, 2H), 2.72 (d, J=4.4 Hz, 3H), 2.08 (s, 3H). MS: m/z=199.00 [M+H].

Step D-2: Preparation of 2-amino-5-chloro-N,3-dimethylbenzamide

A mixture of 6-chloro-8-methyl-2H-benzo[d][1,3]oxazine-2,4(1H)-dione (0.5 g, 2.4 mmol), methylamine hydrochloride (0.32 g, 4.7 mmol) and potassium carbonate (0.33 g, 2.4 mmol) in ethyl alcohol (10 mL) was stirred for 0.5 h at 25° C., and then heated to 80° C. for 5 h. After completion of the reaction, the reaction mixture was poured into ice-water (50 mL). The solid precipitate was filtered off and washed with water (5 mL). The mother liquor was extracted twice with dichloromethane (50 mL). The combined dichloromethane layers were dried over anhydrous sodium sulphate, filtered and evaporated under reduced pressure to get a solid. Both the solids were combined to obtain crude 2-amino-5-chloro-N,3-dimethylbenzamide (0.3 g, 1.5 mmol, Yield: 64%).

Step D-3: Preparation of 2-amino-5-chloro-N,3-dimethylbenzamide

A mixture of 6-chloro-8-methyl-2H-benzo[d][1,3]oxazine-2,4(1H)-dione (0.5 g, 2.4 mmol), methylamine hydrochloride (0.32 g, 4.7 mmol) and pyridine (0.4 ml, 4.7 mmol) in ethyl alcohol (10 mL) was heated at 80° C. for 2 h. After completion of the reaction, the reaction mixture was diluted with water (50 mL) and extracted twice with ethyl acetate (50 mL). The combined ethyl acetate layers were dried over anhydrous sodium sulfate, filtered and evaporated under reduced pressure to get a crude solid. The crude solid was triturated with n-hexane (50 mL) to obtain pure 2-amino-5-chloro-N,3-dimethylbenzamide (0.3 g, 1.4 mmol, Yield: 60%).

The invention claimed is:

1. A single step and single pot process for preparing a compound of Formula V, wherein the process comprises a step (b) of:
   oxidizing and halogenating the dione of Formula II simultaneously into an isatoic anhydride of Formula V using at least one oxidizing reagent and at least one halogenating reagent in the presence of at least one suitable acid;

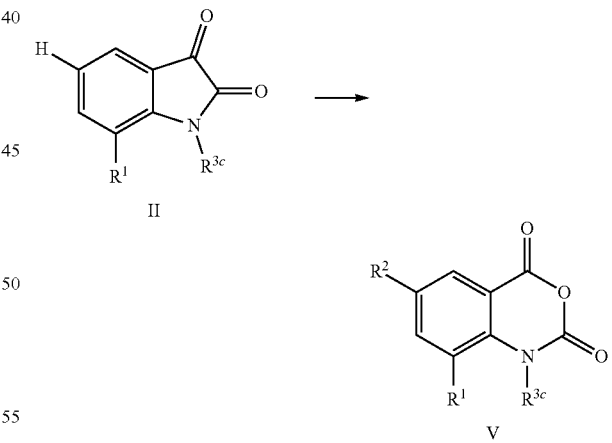

wherein, $R^1$ is $CH_3$, Br or Cl;
$R^2$ is F, Cl, Br, or I;
and
$R^{3c}$ is independently H or $C_1$-$C_4$ alkyl.

2. The process as claimed in claim 1, wherein
   i) the halogenating reagent is HCl, $SOCl_2$, NaOCl and $Cl_2$;
   ii) using at least one suitable oxidizing reagent selected from the group consisting of hydrogen peroxide, m-chloroperbenzoic acid, periodic acid;

iii using at least one acid selected from the group consisting of formic acid, acetic acid, triflic acid, benzoic acid, m-chlorobenzoic acid, trifluoroacetic acid, para-toluene sulfonic acid, methane sulfonic acid, hydrochloric acid, hydroiodic acid, sulphuric acid, and perchloric acid;

iv) at a temperature ranging from 5° C. to 80° C.; and v) using at least one solvent selected from the group consisting of toluene, xylene, t-butyl methyl ether, tetrahydrofuran, 2-methyl tetrahydrofuran, dioxane, monoglyme, diglyme, dichloromethane, chloroform, dichloroethane, N,N-dimethylmethanamide, dimethyl sulfoxide, N-methyl-2-pyrrolidone, and water.

3. The process as claimed in claim 1, wherein i) the oxidizing reagent, and ii) the halogenating reagent are added separately in the sequence in portions to iii) a mixture of the dione of Formula II and the solvent, at a temperature ranging from 10 to 50° C., followed by heating at a temperature ranging from 15-150° C.

4. The process as claimed in claim 1, wherein the process step (b) is carried out i) using a suitable halogenating reagent selected from the group consisting of HX, NaX, KX, CuX$_2$, MgX$_2$, CsX, ZnX$_2$, SOCl$_2$, SO$_2$Cl$_2$, COCl$_2$, X$_2$, C(=O)(OCl$_3$)$_2$, t-BuOCl, NaOCl, chloramine-T, N-halosuccinamides, POX$_3$, PX$_3$, PX$_5$ or metal halides; wherein X is Cl, Br, I or F;

ii) using at least one suitable oxidizing reagent hydrogen peroxide, t-butyl-hydroperoxide, tungstic peroxide, m-chloroperbenzoic acid, benzoyl peroxide, hypohalous acid, ceric ammonium nitrate, hypoceric ammonium nitrate, oxone, periodic acid, hydrogen peroxide urea-adduct, sodium perborate, pyridinium chlorochromate and dimethyl sulfoxide;

iii) using at least one acid selected from the group consisting of formic acid, acetic acid, triflic acid, benzoic acid, m-chlorobenzoic acid, butyric acid, propionic acid, glycolic acid, trifluoroacetic acid, para-toluene sulfonic acid, methane sulfonic acid, butyric acid, citric acid, oxalic acid, malonic acid, maleic acid, gallic acid, tartaric acid, ascorbic acid, hydrochloric acid, hydroiodic acid, sulphuric acid, nitric acid, phosphoric acid, and perchloric acid;

iv) at a temperature ranging from 0° C. to 150° C.; and v) using at least one solvent selected from the group consisting of hexane, heptane, octane, nonane, decane, dodecane, cyclopropane, cyclobutane, cyclopentane, cyclohexane, cycloheptane, cyclooctane, toluene, xylene, mesitylene, benzene, diisopropyl ether, t-butyl methyl ether, tetrahydrofuran, 2-methyl tetrahydrofuran, dioxane, monoglyme, diglyme, methoxy-methane, methoxy-ethane, ethoxy-ethane, di-methoxyethane, di-ethoxyethane, dichloromethane, chloroform, dichloroethane, N,N-dimethylmethanamide, dimethyl sulfoxide, N-methyl-2-pyrrolidone, 1,3-dimethyl-3,4,5,6-tetrahydro-2(1H)-pyrimidinone, hexamethylphosphoramidem, 1,3-dimethyl-2-imidazolidinone and water.

5. The process as claimed in claim 1, wherein the process step (b) is carried out by mixing i) a mixture of the halogenating reagent and the oxidizing reagent, and ii) a mixture of the dione of Formula II and the solvent, at a temperature ranging from 10 to 50° C. and then by heating at a temperature ranging from 15-150° C.

6. The process as claimed in claim 1, wherein the process step (b) is carried out is carried out by adding i) the oxidizing reagent, and ii) the halogenating reagent separately in either sequence in portions or all at once to iii) a mixture of the dione of Formula II and the solvent, at a temperature ranging from 10 to 50° C., followed by heating at a temperature ranging from 15-150° C.

7. The process as claimed in claim 1, wherein i) the halogenating reagent is HBr, NaOBr and Br$_2$;

ii) using at least one suitable oxidizing reagent selected from the group consisting of hydrogen peroxide, m-chloroperbenzoic acid, periodic acid;

iii) using at least one acid selected from the group consisting of formic acid, acetic acid, triflic acid, benzoic acid, m-chlorobenzoic acid, trifluoroacetic acid, para-toluene sulfonic acid, methane sulfonic acid, hydrochloric acid, hydroiodic acid, sulphuric acid, and perchloric acid;

iv) at a temperature ranging from 5° C. to 80° C.; and v) using at least one solvent selected from the group consisting of toluene, xylene, t-butyl methyl ether, tetrahydrofuran, 2-methyl tetrahydrofuran, dioxane, monoglyme, diglyme, dichloromethane, chloroform, dichloroethane, N,N-dimethylmethanamide, dimethyl sulfoxide, N-methyl-2-pyrrolidone, and water.

8. The process as claimed in claim 1, wherein said process further comprises the process for preparing a compound of Formula VII,

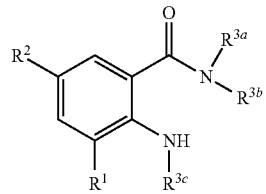

wherein,

R$^1$ is CH$_3$, Br or Cl;

R$^2$ is F, Cl, Br, or I;

R$^{3a}$ and R$^{3b}$ are independently H, C$_1$-C$_4$ alkyl or C$_3$-C$_6$ cycloalkyl-C$_1$-C$_4$ alkyl;

R$^{3c}$ is H or C$_1$-C$_4$ alkyl;

said process comprising the steps of:

a) obtaining a dione of Formula II by reacting a compound of Formula III, chloral hydrate of Formula IV and hydroxyl amine in the presence of at least one suitable reagent;

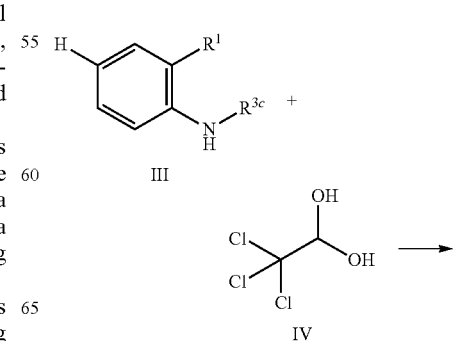

-continued

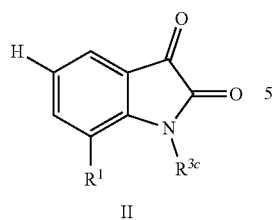

II or obtaining the dione of Formula II by cyclizing a compound of Formula IIIa in the presence of at least one suitable reagent;

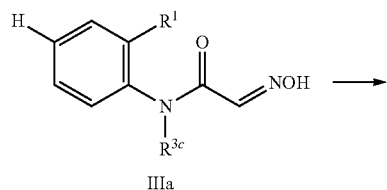

IIIa

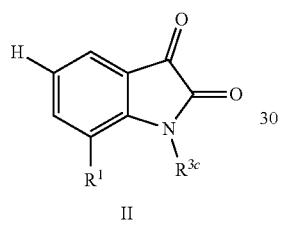

II wherein the compound of Formula IIIa is obtained as an intermediate in the process step of reacting the compound of Formula III, chloral hydrate of Formula IV and hydroxyl amine in the presence of at least one suitable reagent;

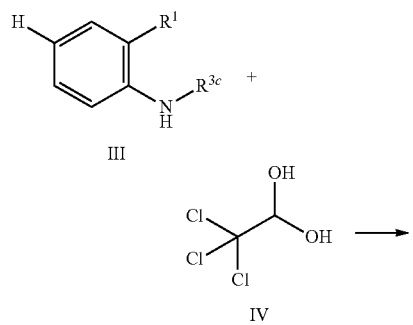

IIIa wherein, $R^1$ and $R^{3c}$ are as defined herein before, b) oxidizing and halogenating the dione of Formula II simultaneously into an isatoic anhydride of Formula V using at least one oxidizing reagent and at least one halogenating reagent in the presence of at least one suitable acid;

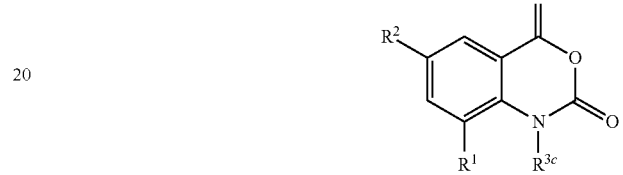

wherein, $R^1$, $R^2$ and $R^{3c}$ are as defined herein before, c) reacting the compound of Formula V with an amine of Formula VI to obtain a compound of Formula VII in the presence of at least one suitable reagent;

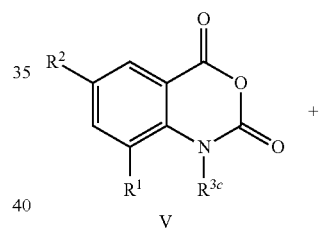

V

+

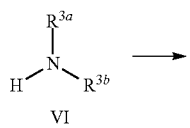

VI

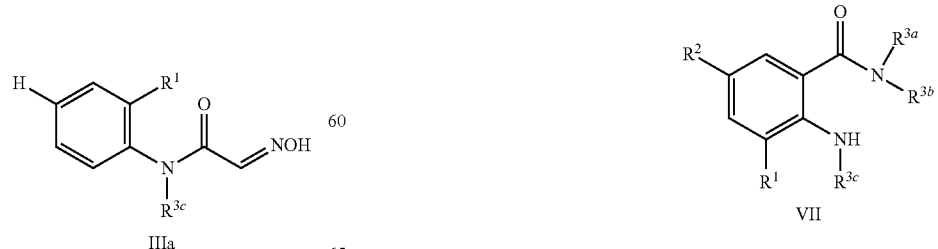

VII wherein, $R^1$, $R^2$, $R^{3a}$, $R^{3b}$ and $R^{3c}$ are as defined herein before.

9. A process for preparing anthranilic diamide of Formula I,

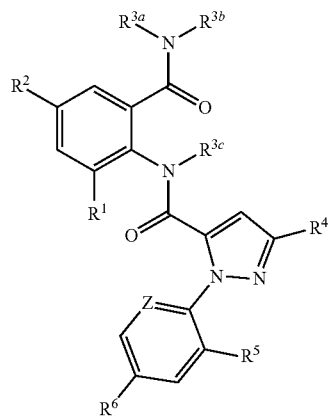

wherein,
R$^1$ is CH$_3$, Br or Cl;
R$^2$ is F, Cl, Br, or I;
R$^{3a}$ and R$^{3b}$ are independently H, C$_1$-C$_4$ alkyl or C$_3$-C$_6$ cycloalkyl-C$_1$-C$_4$ alkyl;
R$^{3c}$ is H or C$_1$-C$_4$ alkyl;
R$^4$ is Cl, Br, CF$_3$, OCF$_2$H, OCH$_2$CF$_3$,

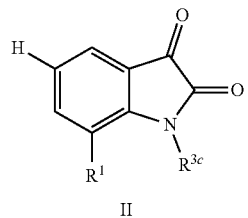

R$^5$ is F, Cl or Br;
R$^6$ is H, F or Cl;
Z is CR$^7$ or N; and
R$^7$ is H, F, Cl or Br,
said process comprising the steps of:
a) obtaining a dione of Formula II by reacting a compound of Formula III, chloral hydrate of Formula IV and hydroxyl amine in the presence of at least one suitable reagent;

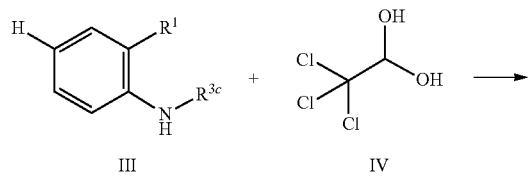

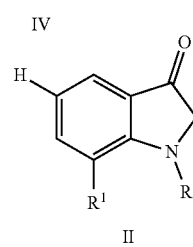

or
obtaining the dione of Formula II by cyclizing a compound of Formula IIIa in the presence of at least one suitable reagent;

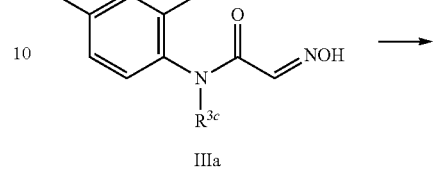

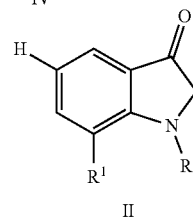

wherein the compound of Formula IIIa is obtained as an intermediate in the process step of reacting the compound of Formula III, chloral hydrate of Formula IV and hydroxyl amine in the presence of at least one suitable reagent;

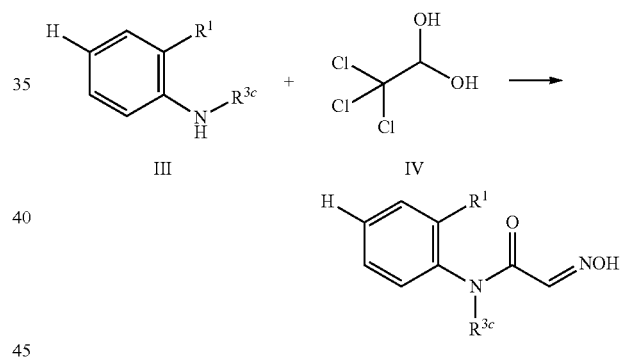

wherein, R$^1$ and R$^{3c}$ are as defined herein before,
b) preparing a compound of Formula V by the single step and single pot process of claim 1,
c) reacting the compound of Formula V with an amine of Formula VI to obtain a compound of Formula VII in the presence of at least one suitable reagent;

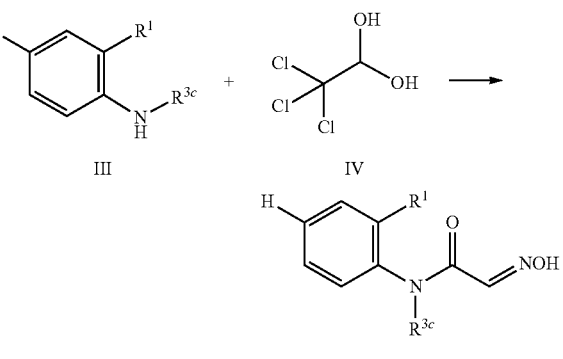

-continued

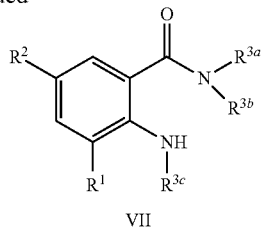

wherein, $R^1$, $R^2$, $R^{3a}$, $R^{3b}$ and $R^{3c}$ are as defined herein before, and d) reacting the compound of Formula VII and a compound of Formula VIII to the compound of Formula I in the presence of at least one suitable reagent;

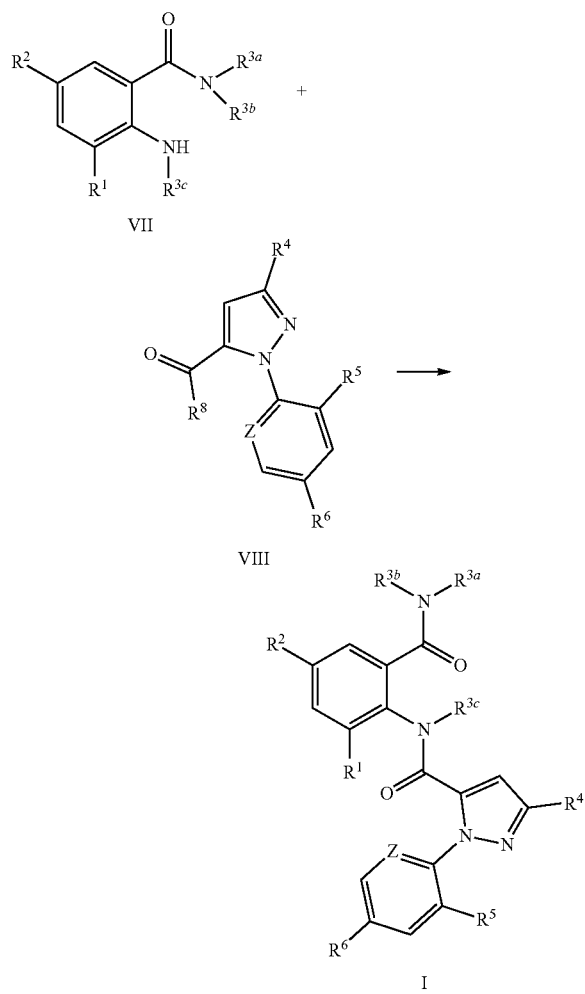

wherein, $R^8$ is OH, Cl, X or O—$C_1$-$C_4$ alkyl; $R^1$, $R^2$, $R^{3a}$, $R^{3b}$, $R^{3c}$, $R^4$, $R^5$, $R^6$ and Z are as defined herein before, and wherein, the compound of Formula V may or may not be isolated.

10. The process as claimed in claim 9, wherein the process step (a) is carried out
   i) using at least one suitable reagent selected from the group consisting of hydrochloric acid, sulfuric acid, acetic acid, trifluoroacetic acid, nitric acid, and sodium sulphate;
   ii) at a temperature ranging from 0° C. to 150° C.; and
   iii) using at least one solvent selected from the group consisting of hexane, heptane, octane, nonane, decane, dodecane, cyclopropane, cyclobutane, cyclopentane, cyclohexane, cycloheptane, cyclooctane, toluene, xylene, mesitylene, benzene, diisopropyl ether, t-butyl methyl ether, tetrahydrofuran, 2-methyl tetrahydrofuran, dioxane, monoglyme, diglyme, methoxy-methane, methoxy-ethane, ethoxy-ethane, di-methoxyethane, di-ethoxyethane, dichloromethane, chloroform, dichloroethane, N,N-dimethylmethanamide, dimethyl sulfoxide, N-methyl-2-pyrrolidone, 1,3-dimethyl-3,4,5,6-tetrahydro-2(1H)-pyrimidinone, hexamethylphosphoramidem, 1,3-dimethyl-2-imidazolidinone and water.

11. The process as claimed in claim 9, wherein the process step (b) is carried out
   i) using a suitable halogenating reagent selected from the group consisting of HX, NaX, KX, $CuX_2$, $MgX_2$, CsX, $ZnX_2$, $SOCl_2$, $SO_2Cl_2$, $COCl_2$, $X_2$, $C(=O)(OCl_3)_2$, t-BuOCl, NaOCl, chloramine-T, N-halosuccinamides, $POX_3$, $PX_3$, $PX_5$ or metal halides; wherein X is Cl, Br, I or F;
   ii) using at least one suitable oxidizing reagent hydrogen peroxide, t-butyl-hydroperoxide, tungstic peroxide, m-chloroperbenzoic acid, benzoyl peroxide, hypohalous acid, ceric ammonium nitrate, hypoceric ammonium nitrate, oxone, periodic acid, hydrogen peroxide urea-adduct, sodium perborate, pyridinium chlorochromate and dimethyl sulfoxide;
   iii) using at least one acid selected from the group consisting of formic acid, acetic acid, triflic acid, benzoic acid, m-chlorobenzoic acid, butyric acid, propionic acid, glycolic acid, trifluoroacetic acid, para-toluene sulfonic acid, methane sulfonic acid, butyric acid, citric acid, oxalic acid, malonic acid, maleic acid, gallic acid, tartaric acid, ascorbic acid, hydrochloric acid, hydroiodic acid, sulphuric acid, nitric acid, phosphoric acid, and perchloric acid;
   iv) at a temperature ranging from 0° C. to 150° C.; and
   v) using at least one solvent selected from the group consisting of hexane, heptane, octane, nonane, decane, dodecane, cyclopropane, cyclobutane, cyclopentane, cyclohexane, cycloheptane, cyclooctane, toluene, xylene, mesitylene, benzene, diisopropyl ether, t-butyl methyl ether, tetrahydrofuran, 2-methyl tetrahydrofuran, dioxane, monoglyme, diglyme, methoxy-methane, methoxy-ethane, ethoxy-ethane, di-methoxyethane, di-ethoxyethane, dichloromethane, chloroform, dichloroethane, N,N-dimethylmethanamide, dimethyl sulfoxide, N-methyl-2-pyrrolidone, 1,3-dimethyl-3,4,5,6-tetrahydro-2(1H)-pyrimidinone, hexamethylphosphoramidem, 1,3-dimethyl-2-imidazolidinone and water.

12. The process as claimed in claim 9, wherein the process step (b) is carried out by mixing i) a mixture of the halogenating reagent and the oxidizing reagent, and ii) a mixture of the dione of Formula II and the solvent, at a temperature ranging from 10 to 50° C. and then by heating at a temperature ranging from 15-150° C.

13. The process as claimed in claim 9, wherein the process step (b) is carried out is carried out by adding i) the oxidizing reagent, and ii) the halogenating reagent separately in either sequence in portions or all at once to iii) a mixture of the dione of Formula II and the solvent, at a temperature ranging from 10 to 50° C., followed by heating at a temperature ranging from 15-150° C.

14. The process as claimed in claim 9, wherein the process step (c) is carried out
   i) using at least one suitable reagent selected from the group consisting of formic acid, acetic acid, triflic acid, benzoic acid, m-chlorobenzoic acid, butyric acid, propionic acid, glycolic acid, trifluoroacetic acid, paratoluene sulfonic acid, methane sulfonic acid, butyric acid, citric acid, oxalic acid, malonic acid, maleic acid, gallic acid, tartaric acid, ascorbic acid, hydrochloric acid, hydroiodic acid, sulphuric acid, nitric acid, phosphoric acid, perchloric acid, boronic acids, amberlysts, aluminum chloride, zinc chloride, boron trifluoro ether, zinc oxide, titanium tetrachloride, tin chloride, sodium carbonate, potassium carbonate, sodium bicarbonate, potassium bicarbonate, pyridine, N-methyl-2-pyrrolidone, and N,N-dimethylmethanamide;
   ii) at a temperature ranging from 0° C. to 150° C.; and
   iii) using at least one solvent selected from the group consisting of formic acid, acetic acid, triflic acid, butyric acid, propionic acid, benzoic acid, m-chlorobenzoic acid, carbonic acid, glycolic acid, and trifluoroacetic acid optionally in combination with at least one additional solvent selected from the group consisting of hexane, heptane, octane, nonane, decane, dodecane, cyclopropane, cyclobutane, cyclopentane, cyclohexane, cycloheptane, cyclooctane, toluene, xylene, mesitylene, benzene, diisopropyl ether, t-butyl methyl ether, tetrahydrofuran, 2-methyl tetrahydrofuran, dioxane, monoglyme, diglyme, methoxy-methane, methoxy-ethane, ethoxy-ethane, di-methoxyethane, di-ethoxyethane, dichloromethane, chloroform, dichloroethane, N,N-dimethylmethanamide, dimethyl sulfoxide, N-methyl-2-pyrrolidone, 1,3-dimethyl-3,4,5,6-tetrahydro-2(1H)-pyrimidinone, hexamethylphosphoramidem, 1,3-dimethyl-2-imidazolidinone and water.

15. The process for preparing anthranilic diamide of Formula I as claimed in claim 9,

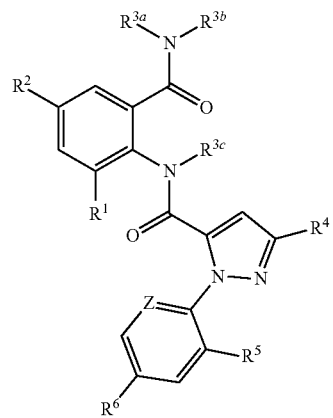

I wherein,
$R^1$ is $CH_3$, Br or Cl;
$R^2$ is Cl;
$R^{3a}$ is H and $R^{3b}$ is methyl or 1-cyclopropyl ethyl;
$R^{3c}$ is H;
$R^4$ is Br,

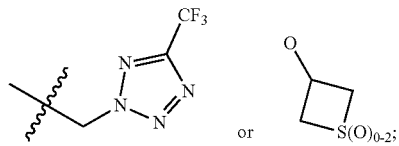

$R^5$ is Cl;
$R^6$ is H or Cl; and
Z is N.

16. The process as claimed in claim 11, wherein X is Cl.

17. The process as claimed in claim 4, wherein X is Cl.

* * * * *